(12) United States Patent
Correa (10) Patent No.: US 6,988,814 B1
(45) Date of Patent: Jan. 24, 2006

(54) ILLUMINATION ASSEMBLY USABLE WITH A PLURALITY OF DEVICES

(76) Inventor: Carlos Correa, 5756 W. Park Rd., Hollywood, FL (US) 33021

( * ) Notice: Subject to any disclaimer, the term of this patent is extended or adjusted under 35 U.S.C. 154(b) by 0 days.

(21) Appl. No.: 10/649,132

(22) Filed: Aug. 26, 2003

Related U.S. Application Data (60) Provisional application No. 60/465,538, filed on Apr. 25, 2003.

(51) Int. Cl.
*F21V 33/00* (2006.01)

(52) U.S. Cl. .................... 362/109; 362/190; 362/191; 362/184; 362/197

(58) Field of Classification Search ........ 362/190–191, 362/109, 285, 396, 438, 800, 119
See application file for complete search history.

(56) References Cited

U.S. PATENT DOCUMENTS 5,797,670 A * 8/1998 Snoke et al. ................ 362/119
6,502,949 B1 * 1/2003 Horiyama et al. .......... 362/119
6,729,743 B2 * 5/2004 Gillette ....................... 362/191
2002/0105797 A1 * 8/2002 Navid et al. ................ 362/120

* cited by examiner

*Primary Examiner*—Ali Alavi
(74) *Attorney, Agent, or Firm*—Malloy & Malloy, P.A.

(57) ABSTRACT

An illumination assembly including one or more light emitting diodes (LED) connected to a power supply and integrated in or supported on a device. When used, a mounting assembly is structured to removably and adjustably dispose the one or more LED's in any one of a plurality of orientations which best facilitates the illumination of a work area of the device on which the illumination assembly is mounted. The light source, power supply and mounting assembly may assume a variety of different structural configurations so as to be readily adaptable to any one of a plurality of devices with which the illumination assembly may be used. The power supply and any one or more of the LED's may be removed and replaced for repair and/or replacement, wherein the versatility of the illumination assembly is such as to be usable with any of a large variety of instruments, mechanical tools or a variety of other utilitarian devices in order to achieve an adequate amount of illumination.

39 Claims, 10 Drawing Sheets

ILLUMINATION ASSEMBLY USABLE WITH A PLURALITY OF DEVICES

CLAIM OF PRIORITY

The present application is based on and a claim to priority is made under 35 U.S.C. Section 119(e) to provisional patent application currently pending in the U.S. Patent and Trademark Office having Ser. No. 60/465,538 and a filing date of Apr. 25, 2003, which is incorporated in its entirety herein by reference.

BACKGROUND OF THE INVENTION

1. Field of the Invention

This invention relates to an illumination assembly structured to be removably and adjustably connected to or integrated within any of a variety of utilitarian devices for purposes of effectively illuminating an intended work area of the device. One or more light sources include one or more light generating elements, preferably in the form of light emitting diodes energized by a contained power supply, wherein the light source and power supply have a sufficiently reduced dimension to be mounted on or incorporated within the various devices.

2. Description of the Related Art

Technology is a major catalyst in the product market. As a practical consequence, many technological advances in a specific area or industry will directly or residually impact other areas in today's modern society. The spectrum related to illumination has enjoyed substantially constant improvement since the advent of the light bulb. The light emitting diode or "LED" is an extremely popular light generating element which has encountered significant improvements in both performance and economy of voltage. The brightness achieved by the technologically advanced LED has expanded its use in areas including taillights on vehicles, flashlights, medical equipment, hobby craft, jewelry, and most especially electronics. However, it is generally recognized that the LED market has not enjoyed the innovative exploitation in certain segments of modern industry. By way of example, devices including medical instruments, mechanical tools, and other utilitarian devices, while frequently requiring illuminated conditions for maximum efficiency, do not often include a self contained or readily adaptable light source. Accordingly, in this industry as well as numerous other market segments, individuals continue to struggle with the use of such devices.

Therefore, it is clear that the need and desirability for an external light source incorporated within an improved illumination assembly would overcome many of the problems currently existing with the use of the utilitarian devices of the type set forth above. Illumination assemblies specifically designed to be used with tools, devices such as tweezers, medical instruments, and the like, while attempting to overcome problems of the type set forth above, have not been completely successful as evidenced by their lack of availability on the commercial market. Problems associated with the use of such known or conventional structures include the location, configuration and/or structuring of known external light sources in a manner which creates shadows due to "back lighting" rather than accomplishing targeted and pinpoint direction of an illumination field on to an intended work area of the instrument in question. Further, the available light structures, particularly those of the type used with utilitarian devices such tools and instruments counter other disadvantages such as being of excessive weight or size thereby frequently interfering with the intended or conventional operation of the device during its use.

By way of example, certain mechanical tools such as, but not limited to a screwdriver structure is known to incorporate a rear-lighted handle base. However, reluctance on the part of the manufacturer or tool designer to completely redesign the overall structural and operative features of such a device results in the existing screwdriver being heavy, bulky and therefore usable for only limited purposes. Understandably, the reluctance on the part of manufactures to completely redesign a line of tools has resulted in the lack of a variety of different instruments, tools, etc. with effective and efficient associated light sources.

Based on the above there is a significant and long recognized need for an illumination assembly either in the form of a removable and adjustable exteriorly mounted structure or an illumination assembly integrated into the tool or instrument itself. Such an improved illumination assembly would provide the desired and effective lighting of a given or intended work area associated with the use of the instrument, tool or device. Further, such an improved illumination assembly should demonstrate sufficient versatility to allow selective orientation or adjustment of the light source, preferably in the form of one or more LED's so as to ensure proper illumination of the work area in question. Further, such an improved illumination assembly should be structured so as to accomplish quick and easy adaptation to a variety of different devices including tweezers, screwdrivers, hex keys, wrenches, ratchets, pens, pencils, magnetic pickups, pliers, drills, saws, mechanical tools of all types, electronic tools as well as numerous other utilitarian devices. In addition, such a preferred and improved illumination assembly should be designed and structured so as to be available to the consuming public at a reasonable cost and not interfere with the intended use or operation of the associated device. Finally, such a preferred illumination assembly should be of a reduced or comparable size and configuration to correspond to that of the device or instrument with which it is used.

SUMMARY OF THE INVENTION

The present invention is directed to an illumination assembly usable with a variety of different devices by being removably and adjustably attached thereto. In alternative preferred embodiments the illumination assembly of the present invention should be structured to be integrated within the structure of the individual device. The versatility of the various preferred embodiments of the present invention is demonstrated by the wide variety of devices with which it may be used. As will be more evident herein after, such devices include mechanical tools, medical instruments, household implements or utensils, and a variety of other utilitarian devices which are normally, but not exclusively, operated by being hand-held. As will also be apparent, certain preferred embodiments of the illumination assembly of the present invention may be more adaptable for use with specific instruments, tools, utensils, etc. than others. By way of example, the structure, size and configuration of certain utilitarian devices render them more easily used with removably and/or adjustably mounted illumination assemblies rather than with the embodiments which are integrated or "built-in" as part of the original formation or manufacture of the tool, instrument or like device.

More specifically, the illumination assembly of the present invention in its various preferred embodiments includes a light source comprising at least one generating element. Substantially all of the embodiments described hereinafter will be represented as using a light emitting diode as the light generating element of the light source. The intended spirit and scope of the present invention is not meant to exclude other types of light generating elements. However, adaptability of the modern day, advanced LED to the various structural modifications of the illumination assembly as used in combination with the diverse instruments or tools as set forth above makes the LED the preferred light generating element to be used.

Accordingly, the light source may comprise at least one LED but in certain preferred embodiments a plurality of LED'S. In addition, a power supply is provided preferably, but not exclusively, in direct association with the light source such as being mounted adjacent thereto and in direct electrical connection therewith. The power supply may take the form of a reduced size battery of the type known in the art and commercially available. Such batteries are extremely small and are replaceable as needed to provide adequate power to the one or more LED's defining the light source. Moreover, the power supply may be cooperatively mounted, positioned or located in a manner such that the light source and the power supply are secured to or mounted on one of the plurality of devices as an integrated unit. However, in at least one preferred embodiment of the present invention the power supply and the light source may be removably connected to one another by virtue of the provision of a "plug-in" type of electrical interface. As with the other operative components of the various embodiments of the illumination assembly, the coupling interface is appropriately dimensioned and disposed and thereby facilitates the removable connection between the power supply and the light source.

Another important feature of at least some of the preferred embodiments of the present invention is the provision of a mounting assembly. The mounting assembly is connected in supporting relation to at least the light source but more preferably to both the light source and the power supply. In each of the corresponding embodiments, the mounting assembly is structured to adjustably secure the light source on the device in a position which facilitates illumination of a predetermined work area thereof. In order to better facilitate a preferred and selective illumination of the predetermined work area, the light source and the mounting assembly are cooperatively structured to facilitate the adjustable positioning of the light source on the device. In addition, certain preferred embodiments of the illumination assembly provide for a selective orientation of the one or more LED's defining the light source relative to the work area to accomplish the aforementioned preferred and effective illumination of the work area.

Accordingly, one embodiment of the mounting assembly of the present invention comprises a sleeve having a hollow interior and terminating in oppositely disposed open ends. The sleeve may be formed of a flexible, at least minimally elastic or expandable material which is dimensioned and configured to provide a gripping type action on the portion of the device to which it is attached. However, it is emphasized that such a gripping engagement will still permit selective positioning of the sleeve, as well as the light source and power supply connected thereto relative to the device on which it is mounted. Such selective positioning allows the light source to be efficiently disposed in the aforementioned preferred orientation to facilitate better illumination of the work area. Therefore, due to the resilient or expandable nature of the material from which at least one embodiment of the mounting sleeve is formed, the sleeve may have a continuous or closed peripheral configuration which facilitates a sliding, surrounding engagement of the mounting sleeve on the device.

As one alternative embodiment to the closed continuous configuration of the sleeve, the sleeve may include an access opening extending substantially along the entire length thereof. The sleeve may then be selectively disposed in either an open or closed position. A closure assembly may be associated with the longitudinal or otherwise peripheral portions of the access opening to maintain it in a closed position thereby assuring its maintenance in an intended, operative location on the device.

Additional alternative embodiments of the mounting sleeve include it being formed from a substantially rigid material dimensioned, configured and otherwise structured to substantially correspond to a portion of the tool, instrument or like device to which it is secured. This latter rigid material embodiment may be best suited for larger instruments such as mechanical tools as will be explained in greater detail hereinafter.

Yet another embodiment of the mounting assembly includes a clip or clamp assembly comprising a support platform for the light source and preferably the power supply. The support platform is connected to two outwardly extending flanges which are at least partially movable relative to the platform. A biasing structure or assembly may be associated with the clamp assembly and may preferably be provided in the form of a biasing spring or member. The biasing member is attachable to the clamp assembly in a manner which normally biases the flanges into at least partially surrounding, gripping engagement with a portion of the device on which it is mounted. Alternatively, the biasing structure can be inherently formed in the platform and flanges due to it being molded by an inherently resilient or flexible material such as plastic, metal, etc.

Another feature of a plurality of the preferred embodiments of the illumination assembly of the present invention include the one or more LED's being movable and therefore adjustable relative to the intended work area, the device on which it is mounted, the mounting assembly and/or other ones of a plurality of LED's directly associated therewith. Such selective adjustability of the one or more LED's further facilitates the orientation thereof into a position which best illuminates the intended or predetermined work area. As should be apparent, such adjustability may be desirable dependent on the configuration, size, overall structure or intended use of the device with which the various embodiments of the illumination assembly are used.

Moreover, the ability to adjustably orient the one or more LED's is further enhanced by the provision of cooperative structures such as an extension assembly. The extension assembly comprises an elongated neck or other structure which provides for the outwardly spaced location of one or more LED's from the mounting assembly with which they are associated. Such an outwardly directed extension structure or assembly may be made from a pliable material or alternatively may be pre-configured and otherwise adjustably positionable relative to the mounting assembly to which it is connected.

As set forth above, additional preferred embodiments of the present invention contemplate various structural modifications of the illumination assembly being integrated within or as part of the utilitarian device itself. Such integrated embodiments may therefore be part of the original manufacture of the instrument, tool, utensil, etc. Accordingly, the light source and more specifically one or more LED's are "built-in" the device and specifically located thereon so as to facilitate the illumination of the intended work area of the device. As a result, the functionality of the device will be greatly enhanced without the requirement of an external light source being attached thereto. Due to the efficiently reduced size and weight of the various components of the plurality of embodiments of the illumination assembly the integration of the light source and power supply, as well as other associated components, are such as to render the illumination assembly of the present invention readily adaptable for such integration at the time of the original manufacture of the device. Accordingly the addition of an "inside" light and its proper location and orientation will have the effect of minimizing shadows frequently caused by the improper positioning of a light source, both internally and externally mounted, as may be known in related areas of endeavor. Also, the power supply in the form of a removable and/or replaceable battery can be disposed within or integrally or otherwise fixedly secured to the appropriate portion of the device, depending on the physical characteristics of the device. Similar to the embodiments described above, the light source may comprise one or more LED's located at the "working end" of the device or at other preferred locations in order to illuminate the aforementioned undesirable creation of shadows or dark areas in the field of the illuminated work area.

Various structural modifications of the integrated embodiments of the illumination assembly include the wiring of the LED's and the power source internally along various parts of the device with which it is used. Also, the securement of the various components of the illumination assembly may be accomplished by an overlying molded plastic or like material covering. The covering may itself contain the entire illumination assembly. As such, the housing, support platform or like structure associated with the placement and storage of the battery may come in different shapes and sizes to compensate for the structure of the device on which it is mounted. However, an important factor is the provision of sufficient brightness and voltage of the required one or more LED's to suit the specific industry standards of a given device.

Yet another preferred embodiment included in the "integrated" category of the illumination assemblies involves the formation of a plastic or other moldable material jacket or shell specifically adapted to conform to all or at least portions of the size and configuration of the device on which the illumination assembly is to be mounted. Moreover, the various operative components of the illumination assembly may be integrated directly in the molded material shell or jacket, wherein the shell is mounted in overlying, covering or otherwise attached relation to the device or to predetermined portions thereof. Such attachment may be by integrated molding, adhesive, inherently formed locking members or tabs or a variety of other applicable means to attach or connect the shell to the intended device.

As with the previously described "add-on" category of illumination assembly embodiments, the "integrated" category of illumination assembly embodiments may also include a light source having one or more LED's. Similarly, one or all of the LED's may be movable and therefore adjustable relative to the intended work area, the device on which it is mounted and/or other of the plurality of LED's defining the light source. Proper and selective orientation of the light source is thereby accomplished in this category of preferred illumination assembly embodiments as also described in greater detail hereinafter.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIGS. 2 and 2a are side views of additional preferred embodiments of the illumination assembly of the present invention incorporating a mounting assembly differing from that of FIGS. 1 and 1a.

FIG. 3 is a combination of the preferred embodiments of the illumination assembly of the present invention as represented in FIGS. 1 through 2a.

FIG. 16 is a perspective view of yet another preferred embodiment of a mounting assembly associated with the illumination assembly of the present invention.

FIG. 16a is a perspective view of the embodiment of FIG. 16 shown in an open position.

FIG. 17 is a perspective view in exploded form of the embodiments of FIGS. 16 and 16a.

FIG. 18 is a perspective view of the embodiment of FIGS. 16, 16A and 17 shown in assembled form.

Like reference numerals refer to like parts throughout the several views of the drawings.

DETAILED DESCRIPTION OF THE PREFERRED EMBODIMENT

Figures 1, 1A:
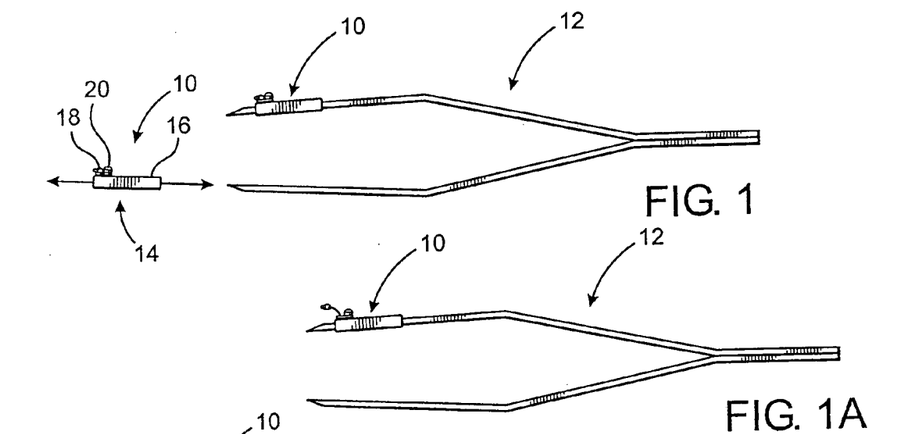
FIGS. 1 and 1a are side views of related preferred embodiments of the illumination assembly of the present invention as applied to a utilitarian device represented by a pair of tweezers.
Figure 2:
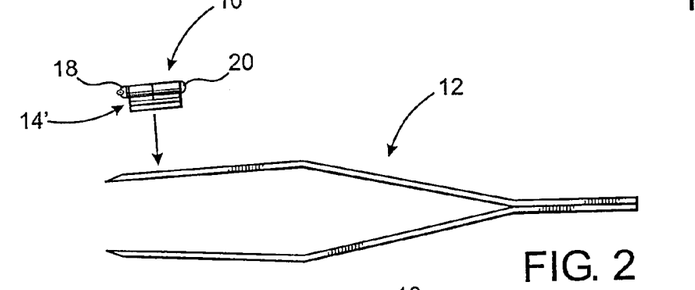
Figure 3:
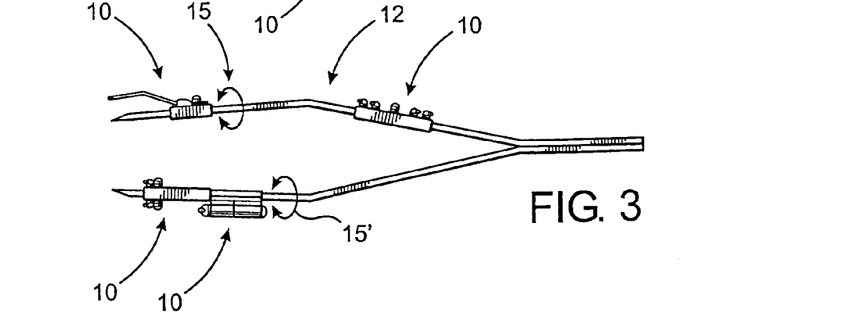
Figure 4:
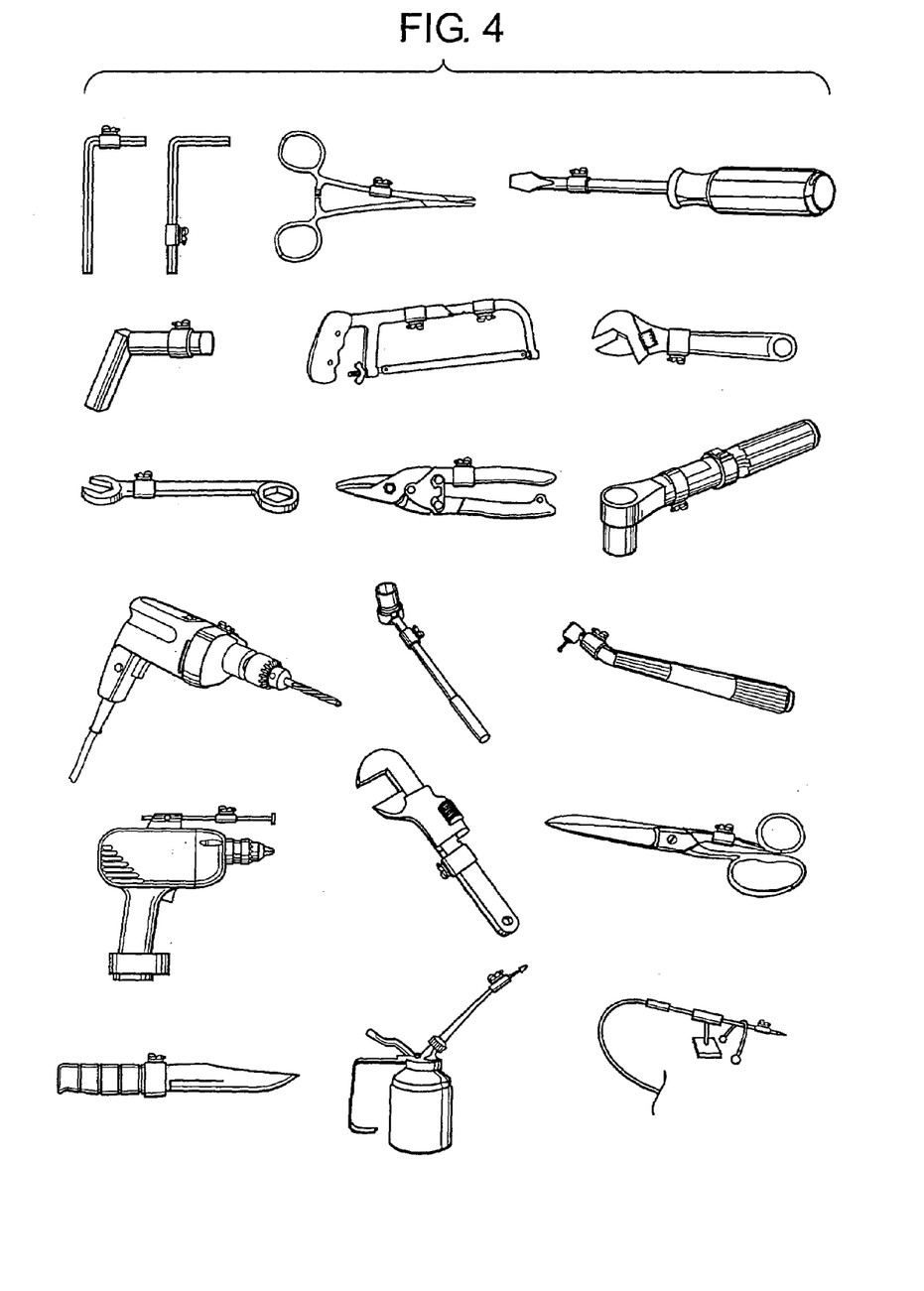
FIG. 4 is a composite view of various embodiments of the illumination assembly of the present invention mounted on or connected to a plurality of different utilitarian devices.

As shown in the accompanying Figures, the present invention is directed towards an illumination assembly generally indicated as 10 structured to be removably and adjustably connected to or mounted on any one of a wide variety of utilitarian devices generally indicated as 12 in FIGS. 1 through 3. For purposes of clarity, various types of devices with which various embodiments of the illumination assembly 10 may be used are represented in composite form in FIG. 4. Such devices include wrenches, screwdrivers, saws, pliers, tire gauges, knives, containers, drills, scissors, medical instruments, etc. It is emphasized that the composite representation of FIG. 4 is not meant to be all inclusive but rather it is representative of an even larger number of devices typically, but not necessarily, operative while being hand held.

In order to simplify and further clarify the structural and operational details of the illumination assembly 10 of the present invention, its removable and adjustable attachment, as shown in FIGS. 1 through 3 as well as its integration into a device 12' will be represented wherein the device 12 and 12' will be consistently presented as a pair of tweezers. However it is again emphasized that each of the preferred embodiments of the illumination assembly 10 of the present invention can be adapted with little or no structural modification for use on any of an extremely large number of utilitarian devices of the type, but not limited to, those disclosed in the composite of FIG. 4. Further, the specific structural components of each of the plurality of preferred embodiments of the illumination assembly 10 will be described in greater detail with specific reference to FIGS. 5 through 37. However, it is recognized that for purposes of a detailed description, the illumination assembly having various structural modifications representative of and at least partially defining the plurality of preferred embodiments, will be consistently represented in the accompanying Figures as reference numeral "10".

Figure 2A:
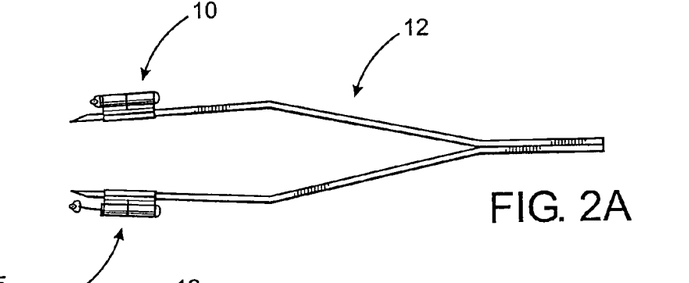

Therefore, with primary reference to FIGS. 1 and 1a, the illumination assembly 10 comprises a mounting assembly generally indicated as 14 preferably in the form of a sleeve 16 disclosed and to be described in detail with reference to FIGS. 5 through 15. A light source 18 and a power supply 20 are mounted on or connected to an exterior of the mounting assembly 16. When applied to the device 12 the illumination assembly 10 is fitted thereon by removably and adjustably positioning the mounting assembly 14 at an appropriate location relative to a predetermined and/or intended work area. It is of course to be understood that the intended work area will differ dependant upon the type of the device 12 as well as its intended use and application. Therefore, the specific location of the illumination assembly 10 may vary greatly in order to accomplish a maximum or appropriate level of illumination of the intended work area. With reference to FIGS. 2 and 2a, the illumination assembly 10 comprises a mounting assembly 14' which differs from that of the embodiment of FIGS. 1 and 1a and which will be described in greater detail in herein after with specific reference to FIGS. 17 through 22. However, common to both the mounting assemblies 14 and 14' is the ability to be removably and adjustably mounted on or connected to any of a plurality of different portions of a device 12 in order to most effectively illuminate a predetermined work area of the device 12.

As shown in FIG. 3 the device 12, again depended upon its use and structural or physical characteristics, may include a plurality of different types of illumination assemblies 10. The individual illumination assemblies 10 include different ones of the mounting assemblies 14 and 14' as well as modifications both in structure, quantity and placement with the various light sources 18. However, it is emphasized in each of the preferred embodiments of the present invention the light source 18 may include at least one but in many instances a plurality of light generating elements. Further, as will be emphasized throughout the description of the present invention, the one or more light generating elements are preferably defined by light emitting diodes (LED). Each of the light generating elements or LED's may differ in their structure and operational performance by being either fixed or adjustable as described in greater detail with specific reference to FIGS. 26 through 37.

Therefore, as generally represented in the embodiments of FIGS. 1, 1a, 2, 2a and 3, any number of utilitarian devices may include one or more illumination assemblies 10. Further, each of the one or more illumination assemblies 10 may include a light source having one or more LED's and one or more power supplies electrically connected thereto so as to provide operative energy for the activation of the one or more LED's. Each of the one or more LED's may be either fixed or adjustable into a preferred orientation, relative to the intended work area of the device 12, the mounting assembly 14 or 14' to which they are connected as well as others of a plurality of LED's associated with the same illumination assembly 10.

Figure 5:
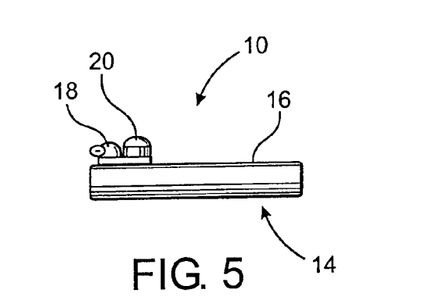
FIG. 5 is a side view of a preferred embodiment of the illumination assembly of the present invention including a mounting assembly in the form of a sleeve.
Figure 6:
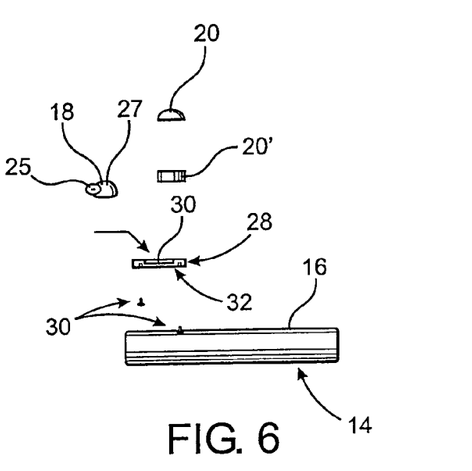
FIG. 6 is a an exploded view of the various components associated with the embodiment of FIG. 5.

With primary reference to FIGS. 5 through 15 the sleeve 16 of the mounting assembly 14 comprises a substantially hollow interior 19 and two oppositely disposed open ends. The sleeves 16 may include structural modifications which may be considered additional preferred embodiments of the illumination assembly 10 of the present invention. However, common to each of the sleeves 16, 16' 16" and 16''', the light source 18 and the power supply 20 are mounted on an exterior surface or other exposed portion thereof. As shown in FIG. 6, the light source 18 includes at least one LED 25 secured to a mount 27 which itself may assume a variety of different structural configurations, sizes, etc. The power supply 20 may be secured to a base or housing 20', wherein both the light source 18 and the power supply 20 are secured to a common support platform 28 in substantially adjacent relation to one another.

An electrical conductor or other appropriate means of establishing electrical interconnection between the power supply 20 and the light source 18 may be incorporated within the platform 28, as at 30, or may be separate therefrom. Also, attachment or other disposition of the light source 18 and power supply 20 may be accomplished by securing the support platform 28 by means of individual, separate connectors 30 fitted into or cooperatively structured to be received at or about socket or recess areas 32 formed in the platform 28. It is also to be noted that a variety of other appropriate means of attachment of the platform 28 to the mounting assembly 12 can be utilized such as adhesive, heat welding, etc.

Figure 7:
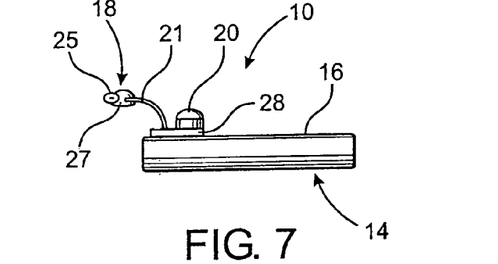
FIG. 7 is a side view of the illumination assembly of the present invention similar to the embodiment of FIG. 5 and including a different light source structure.

As represented in the preferred embodiment of FIG. 7 various operative components of the illumination assembly 10 can vary and still be incorporated within the intended spirit and scope of the present invention. More specifically, the light source 18, may include a connector 31 having one or more LED's 25 secured thereto and being disposed in an outwardly, easy adjustable location relative to the platform 28 and the mounting assembly 14. This outwardly disposed connector 31 may be in the form of a pliable, wire or arm-like attachment which, due to its pliable nature facilitates the selective orientation of the light source 18 in any of a number of different positions to accomplish appropriate illumination of the work area.

Figure 8:
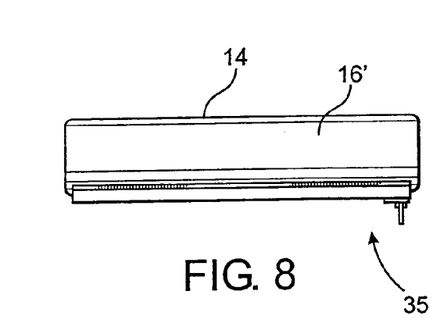
FIG. 8 is a side view of yet another embodiment of the sleeve mounting assembly as represented in FIGS. 5 through 7.
Figure 9A:
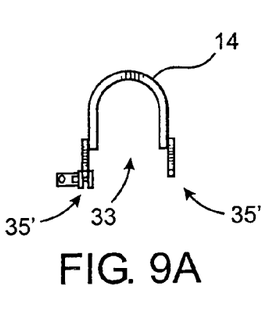
FIGS. 9a and 9b are end views of the embodiment of FIG. 8 shown respectively representing open and closed positions.
Figure 9B:
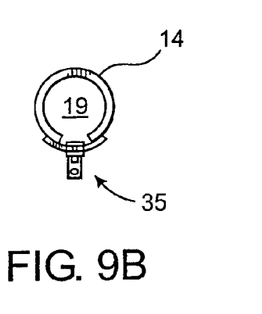
Figure 10:
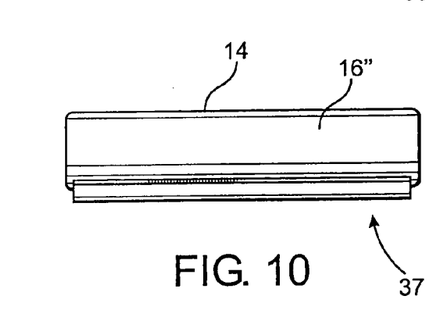
FIG. 10 is a side view of yet another embodiment of the sleeve mounting assembly of the present invention.
Figure 11A:
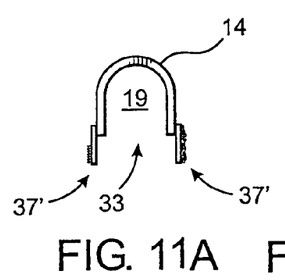
FIGS. 11a and 11b are end views of the embodiment of FIG. 10 respectively representing open and closed positions thereof.
Figure 11B:
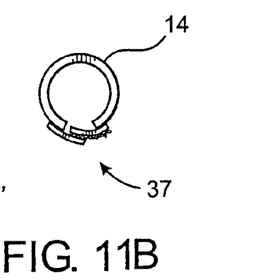

FIGS. 8, 9a and 9b disclose yet another preferred embodiment of the sleeve 16' which includes an access opening 33 extending along its length. A closure 35 is connected to or otherwise directly associated with the access opening 33 such as by being secured to peripheral edges or portions thereof as at 35'. Similarly, the embodiment of FIGS. 10, 11a and 11b disclose the sleeve 16" having an access opening 33 extending along the length thereof, wherein the closure assembly 37 is in the form of a hook and loop type fastener or other easily removably attachable fastener structure facilitating the opening and closing of the access opening 33. Similar to the embodiment of FIGS. 9a and 9b, the hook and loop type fastener 37 may be secured to opposite peripheral or adjacent portions of the access opening 33 as at 37'. As clearly shown in FIGS. 9a and 9b and 11a, 11b provision of the access opening 33 and the respective closure assemblies 35 and 37 facilitate the sleeve 16' and 16" being selectively disposed between an open position (9a and 11a) and a closed position (9b and 11b). Accordingly, when in the open position, an appropriate portion of the device 12 to which the illumination assembly 10 is attached may pass transversely through the access opening 33. Thereafter, the sleeve-like closure assembly 14 is disposed in its closed position so as to substantially surround and at least partially enclose a corresponding portion of the device 12 to which it is attached.

Figure 12:
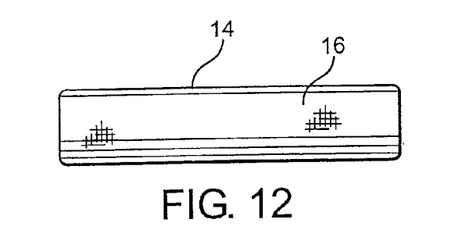
FIG. 12 is a side view of the embodiment of the mounting assembly as shown in FIGS. 5 through 7.
Figure 13:
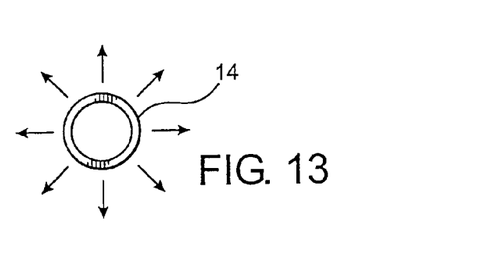
FIG. 13 is an end view of the embodiment of FIG. 12 schematically representing the sleeve mounting assembly formed from a resilient or expandable material.

FIG. 12 represents the preferred embodiment of the sleeve 16 of closure assembly 14 as demonstrated in FIGS. 5 through 7. More specifically, the sleeve 16 may be formed of a flexible, at least minimally elastic material. As demonstrated by the directional arrows of FIG. 13, the sleeve 16 can expand outwardly, if needed, to accommodate the size and other structural characteristics of the portion of the device 12 to which it is attached. Such elastic qualities of the sleeve 16 enable it to be removably secured to various portions of the device 12 where appropriate, while at the same time allowing it to be easily adjustable either along its length or rotationally as demonstrated by the appropriate directional arrows 15 of FIG. 3. However, it should also be noted that the sleeve 16, when intended for use on somewhat larger devices than the representative tweezers of the accompanying drawings, may be formed from a rigid or semi-rigid material to facilitate the stability of the illumination assembly 10 when connected to such a larger device.

Figure 14:
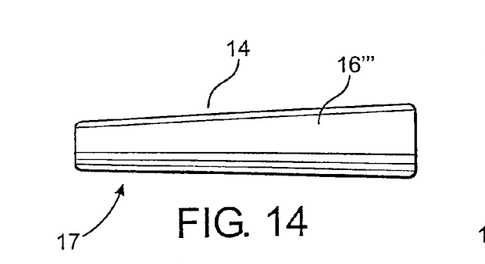
FIG. 14 is yet another preferred embodiment of the sleeve mounting assembly of the present invention.
Figure 15:
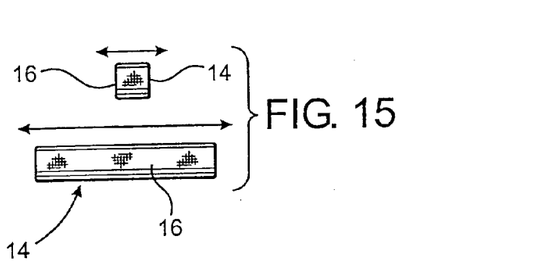
FIG. 15 is a composite view representing the sleeve mounting assembly in a plurality of different lengths.

Additional structural modifications of the sleeve 16''' include a tapered configuration generally indicated as 17. As represented in FIG. 14, at least one of two oppositely disposed open ends communicating with the hollow interior 19 may be tapered so as to better conform to the dimension or configuration of the device to which it is connected. The sleeve 16''' may also be formed of either a flexible, at least minimally elastic material as with the embodiment of FIG. 12 or may be formed of a rigid or semi-rigid material as described above. Further, any of the embodiments of FIGS. 8 through 14 may vary in length as demonstrated by the composite representation of FIG. 15. The preferred length of the sleeve 16 will of course be dependant upon the device to which it is attached including its size, configuration, placement of the mounting assembly 14 and the intended use of the device.

Figures 16, 16A, 17, 18:
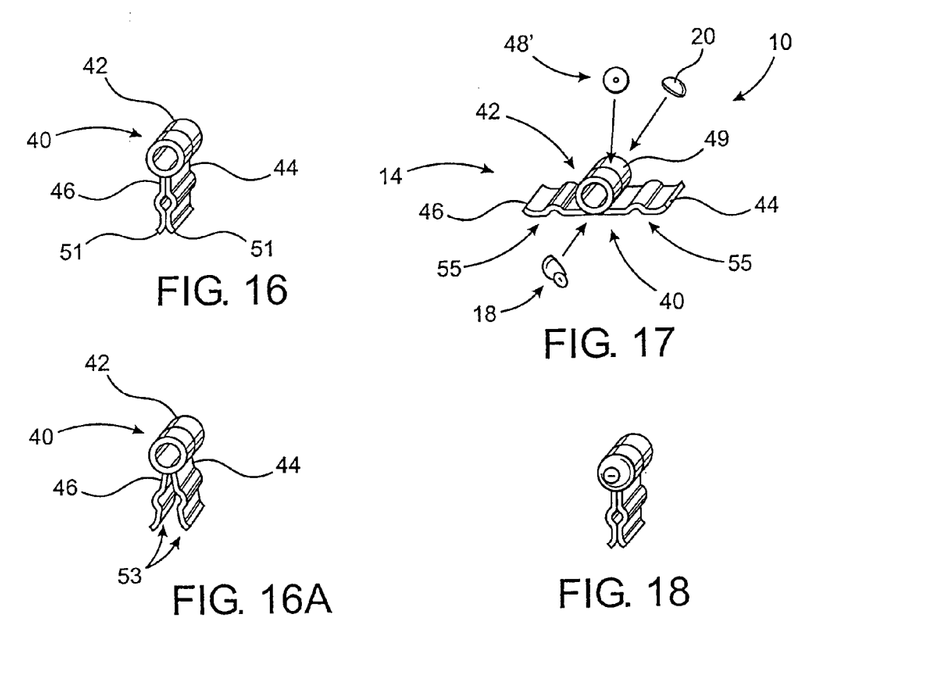
Figure 19:
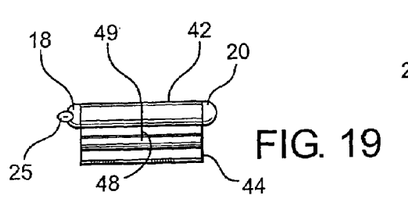
FIG. 19 is a side view of the embodiment of FIG. 18.

With primary reference to FIGS. 16 through 22, the mounting assembly 14, as set forth above with reference to FIGS. 2 and 2a may differ from the sleeve 16 as described in detail with reference to FIGS. 5 through 15. More specifically, the mounting assembly 14 of the embodiment of FIGS. 17 through 22 comprises a clamp assembly 40 having a support platform which may be in the form of an elongated, substantially cylindrical housing 42 and a plurality of flanges. There is preferably provided two flanges 44 and 46 movable relative to the housing 42 and extending outwardly therefrom. As shown in the embodiments of FIGS. 17 through 19, when the housing 42 is defined by a continuous cylindrical configuration extending along substantially the entire length of the clamp assembly 40, the light source 18 and the power supply 20 may be secured to opposite ends thereof. However, the dimension, configuration and location of the cylindrical housing 42 may vary as at 42' in the embodiments of FIGS. 21 and 22 such that the light source, including one or more LED's 25 may be connected adjacent to the housing 42' such as on a support platform 28' similar to that described with the embodiments of FIGS. 5 through 7.

Figure 20:
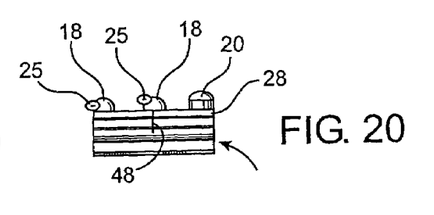
FIG. 20 is a side view of the closing assembly of the embodiment of FIGS. 16 and 16a including structural modification of a light source associated therewith.
Figure 21:
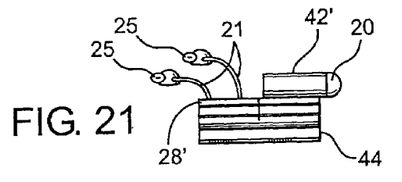
FIG. 21 is a side view similar to the embodiment of FIG. 20 showing an additional structural modification of a light source associated therewith.
Figure 22:
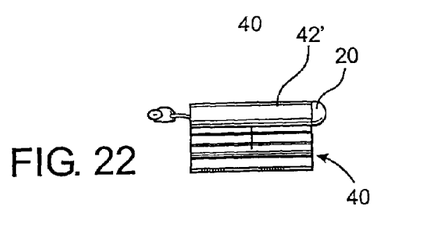
FIG. 22 is a side view similar to the embodiment of FIG. 21 showing yet another structural modification of a light source associated therewith.

Alternatively, FIG. 20 discloses the flat or other non-cylindrical configuration of the support platform 28 while still being associated directly with and defining a portion of the clamp assembly 40 including the outwardly extending flanges 44 and 46. Other structural features associated with the clamp assembly 40 as demonstrated in the embodiments of FIGS. 16 through 18 include the provision of a biasing assembly. In the embodiment of FIG. 17 the biasing assembly comprises at least one biasing spring or like member 48 attached to and made apart of the clamp assembly by being disposed in biasing engagement with the flanges 44 and 46. More specifically, the biasing member 48 may be disposed in receiving relation within a recess or formed groove 49. In such a position, corresponding portions of the biasing member 48 engage and tend to normally bias the flanges 44 and 46 into a closed or gripping position demonstrated in FIG. 16. Due to the fact that the flanges 44 and 46 are at least minimally movable relative to the housing and support platform 42, 28 the flanges 44 and 46 may be separated to accommodate and receive an appropriate portion of a device 12 as clearly represented in FIGS. 2, 2a and 3, as set forth above. Further the flanges 44 and 46 may include initially separable peripheral portions or lips as at 51 to facilitate the spreading of flanges 44 and 46 and access to the interior thereof as indicated by directional arrows 53.

Also in at least one preferred embodiment one or more of the flanges 44 and 46 may include indentations or groove segments 55 formed therein such that a portion of the device 12 to which they are attached, such as the leg of tweezer as demonstrated in FIGS. 2 and 2a will be received in a stable manner within such grooves 55. It should be apparent that through action of the biasing means, such as the biasing member 48, the flanges 44 and 46 are biased into a gripping or clamping engagement with a corresponding portion of the device 12. Such a gripping or clamping action still allows for the longitudinal sliding placement or positioning of the corresponding illumination assembly 10 on various portions of the device 12 and/or alternatively allows for the rotation thereof as demonstrated by directional arrow 15' of FIG. 3.

It should be further noted that the aforementioned biasing means may take the form of an "inherent bias" such as by the clamp assembly 40 being formed from a moldable, inherently resilient material such as plastic, metal, etc. As such the flanges 44 and 46, while still being movable relative to the housing 42 or support platform 28, are inherently biased into the closed position of FIG. 16. Separation of the flanges 44 and 46 may occur due to the spread lip configuration of 51 to at least temporarily dispose the flanges 44 and 46 into the open position of FIG. 16a. The open position facilitates placement of a corresponding portion of the device 12 into the interior of the clamp assembly 40 as indicated by directional arrows 53.

Figure 23:
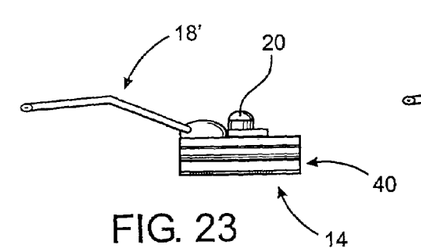
FIG. 23 is a side view representing a closure assembly of the embodiment of FIGS. 16 and 16a and including yet another structural modification of the light source associated therewith.
Figure 24:
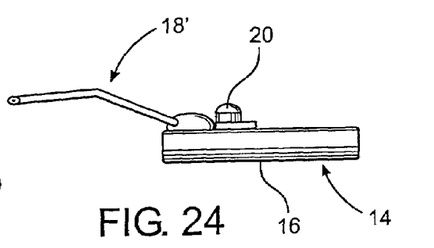
FIG. 24 is a side view of yet another preferred embodiment of FIG. 23 but incorporating the closure assembly of FIG. 12.
Figure 25:
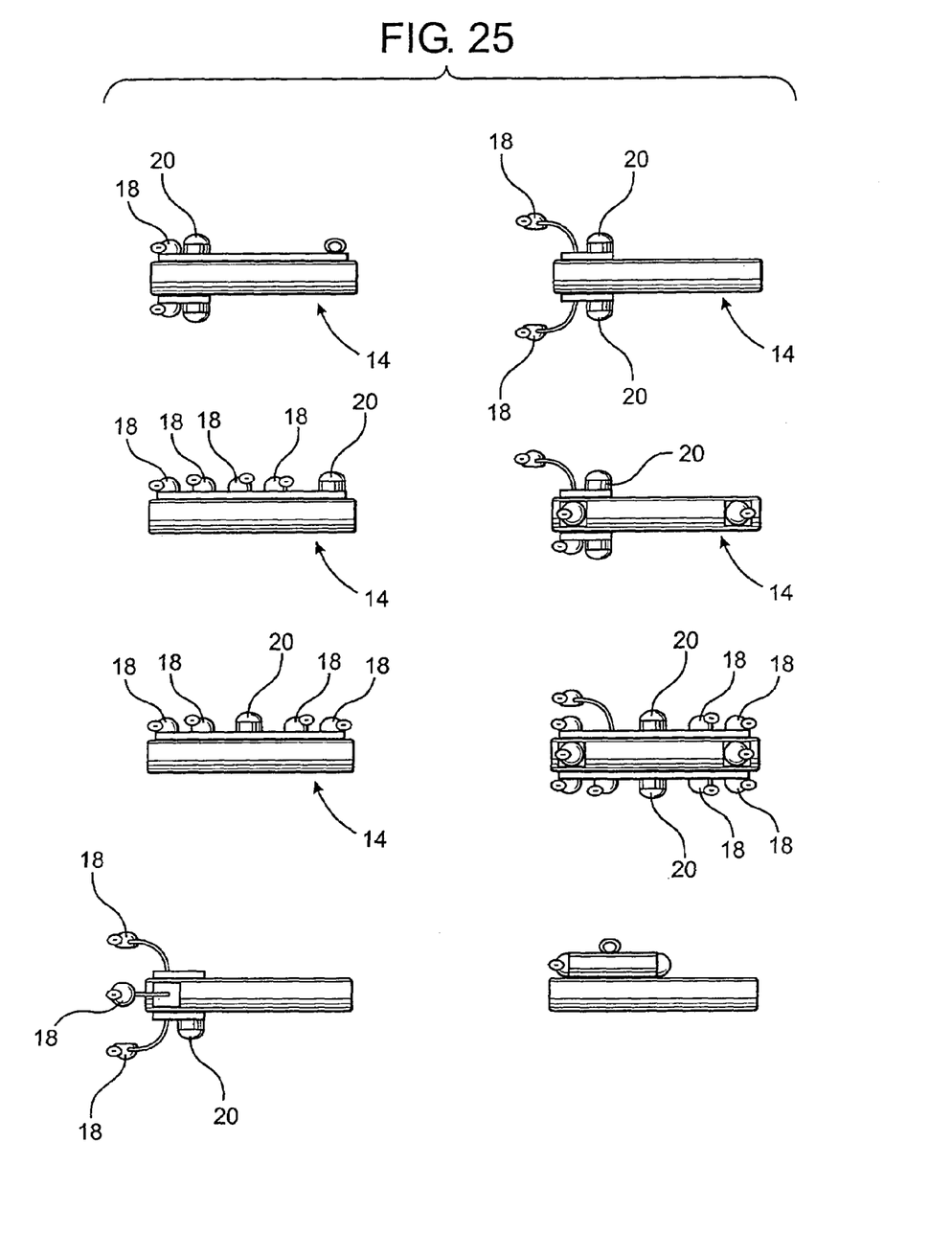
FIG. 25 is a composite view showing the closure assembly of the embodiment of FIG. 12 and incorporating a variety of different structural modifications of a light source and power supply which may be associated therewith.

With reference to FIGS. 23 and 24 the versatility and structural adaptability of the various preferred embodiments of the illumination assembly 10 is demonstrated by the power supply 20 and a variety of different light sources 18' being mounted on different ones of the mounting assemblies 14 such as the clamp assembly 40 and the sleeve 16. The preferred embodiments of the light source is indicated as 18' in FIGS. 23 and 24 will be described in greater detail with specific reference to FIGS. 31 through 36. FIG. 25 represents a composite of a plurality of various structural modifications each defining yet additional preferred embodiments of the illumination assembly 10 of the present invention. As disclosed, a mounting assembly 14 which may be in the form of sleeve 16 or clamp assembly 40 may be disposed in supporting, connecting relation to a variety of different combinations of light sources 18 and power supplies 20. Further as will be explained in even greater detail with reference to FIGS. 26 through 28 the various light sources 18, including one or more LED's 25, may be fixed or adjustably/movably supported relative to a corresponding one of the mounting assemblies 14 such that either or both the mounting assembly 14 and/or the individual light sources 18 and one or more LED's 25 associated therewith, facilitate the adjustable positioning of the light source 18 as well as the selective orientation of the one or more LED's 25 relative to the work area of the device 12, which is intended to be illuminated.

Such selective orientation and adjustable positioning of the light source 18 is further demonstrated in the structural features of the preferred embodiments of FIGS. 26 through 30. More specifically, FIG. 26 discloses a light source 18 which is capable of both rotational movement as indicated by directional arrow 60 and linear, pivotal or twisting movement as indicated by directional arrow 62. In accomplishing such universal type movement an attendant orientation of the LED 25 as well as the overall light source 18, the mount 50 includes a cap or head portion 52 removably secured to a base 54 preferably by means of a "snap-fit" type of connection. Such snap-fit connection is accomplished by cooperative dimensioning and positioning of corresponding peripheral edges 52' and 54' disclosed in FIG. 27. Therefore, the head or cap 50 may be "press fitted" onto the base 54 wherein sufficient tolerances are built into the peripheral portions 52' and 54' to facilitate the snap-fit connection while still allowing for the rotational and pivotal or twisting movement 60 and 62 respectively.

As represented, the cap 52 is rotational as indicated by directional arrow 60, relative to the base 54 while concurrently allowing the vertical or other directional twisting or pivoting of the LED 25 relative to the cap 52 and base 54 as indicated by directional arrows 62. The aforementioned rotational, pivotal twisting or like movement of the LED 25 is accomplished by a pin and hinge type of attachment utilizing conventional or customized connector members 57. Therefore, the LED 25 and cooperative components of the light source 18 can be said to move concurrently in substantially transverse axes defined by the rotational axes of the head 52 relative to base 54 and the pivotal axes at least partially defined by the connecting pin of the connector members 57 represented in FIG. 27.

Figure 26:
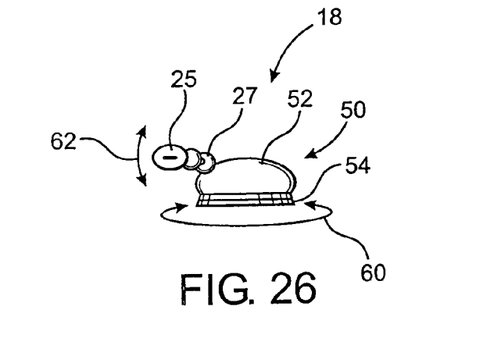
FIG. 26 is a detailed view in perspective showing yet another preferred embodiment of a light source of the illumination assembly of the present invention.
Figure 27:
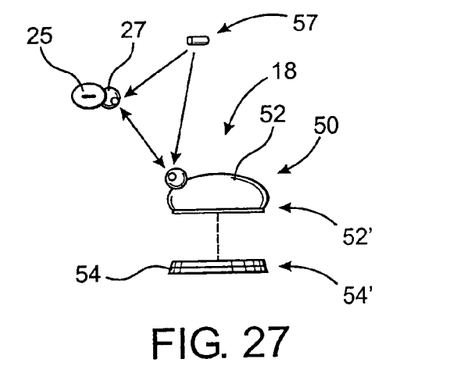
FIG. 27 is an exploded view of the embodiment of FIG. 26.
Figure 28:
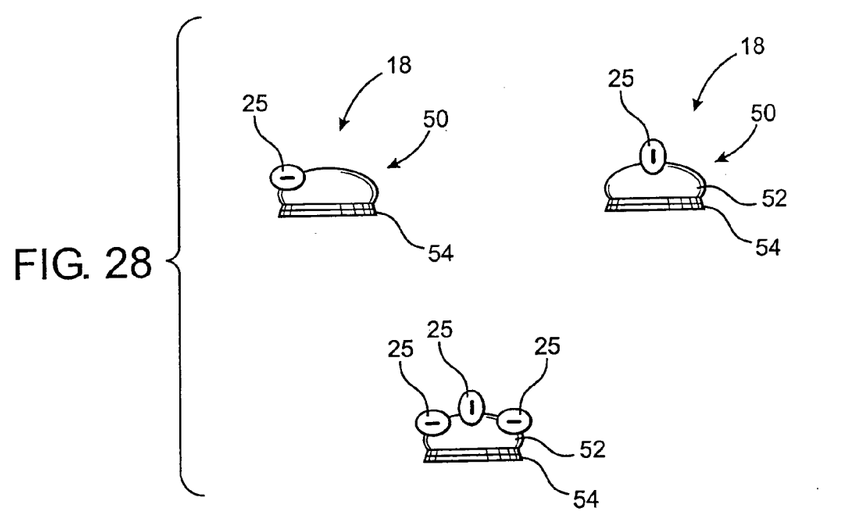
FIG. 28 is a composite view showing the various structural modifications of a light source of the illumination assembly of the present invention.
Figure 29:
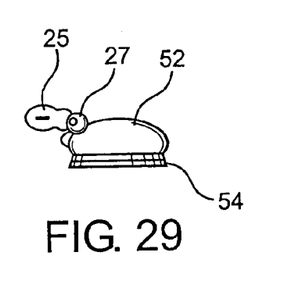
FIG. 29 is yet another preferred embodiment of the light source of the illumination assembly of the present invention.
Figure 30:
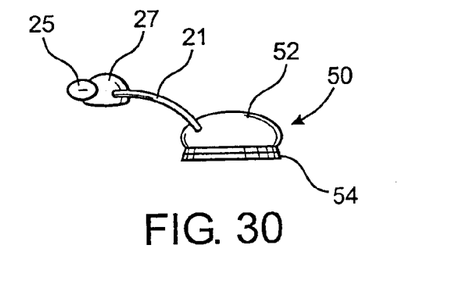
FIG. 30 is a side view of yet another preferred embodiment of the light source of the illumination assembly of the present invention.

FIGS. 28 through 30 represent other structural modifications of the light source 18, wherein the cap or head 52 is fixedly secured to the base 54 and/or movable thereto as represented in FIG. 27 and further wherein one or more LED's 25 may be fixedly secured to the cap 52 in a variety of different locations as indicated by the composite of FIG. 28. In addition, FIG. 29 shows that the head or cap 52 is fixed relative to the base 54 and the LED 25 and mount 27 are interconnected by the hinge type connectors 57 (FIG. 27) to accomplish the reciprocal pivotal movement demonstrated by directional arrows 62 in FIG. 26. Somewhat similarly, the embodiment of FIG. 30 has been at least briefly described above a providing a fixed or movable interconnecting cap 52 and base 54 supporting LED 25 and mount 27 by means of an outwardly extending pliable material connecting arm or like structure 21.

Figure 31:
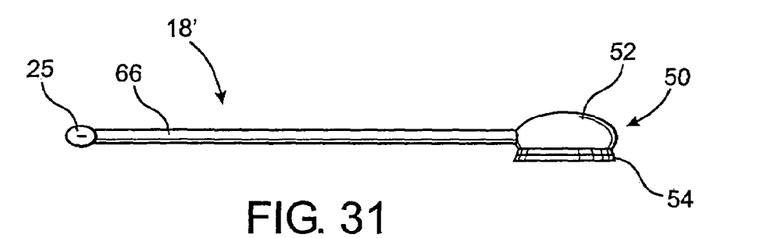
FIG. 31 is yet another preferred embodiment of the light source of the illumination assembly of the present invention.
Figure 32:
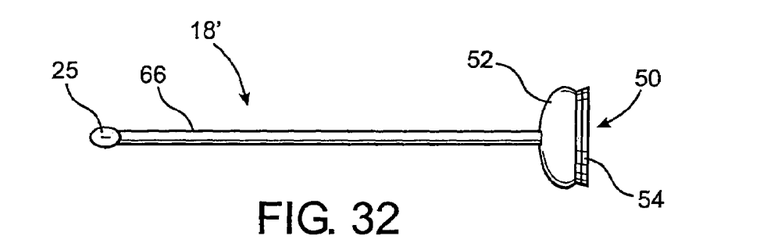
FIG. 32 is yet another preferred embodiment of a light source of the illumination assembly of the present invention.
Figure 33:
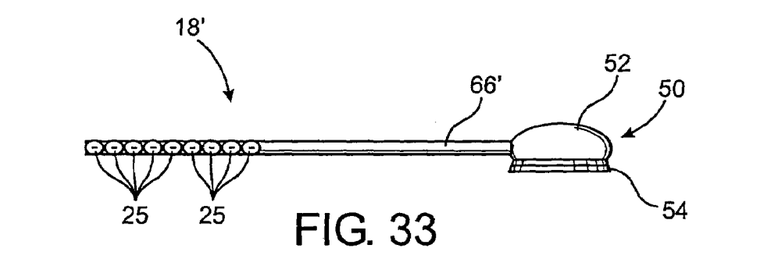
FIG. 33 is yet another preferred embodiment of a light source of the illumination assembly of the present invention.
Figure 34:
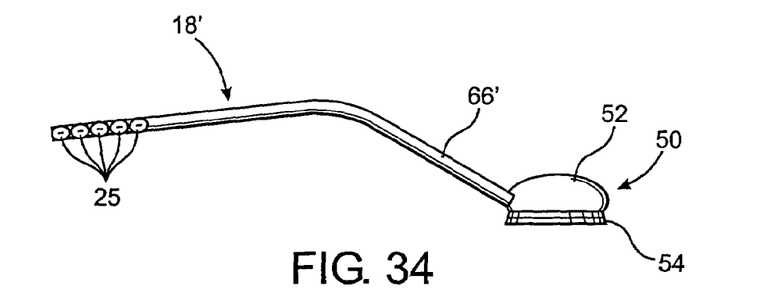
FIGS. 34 and 35 are side views similar to the embodiment of FIG. 3 incorporating a different structural configuration.
Figure 35:
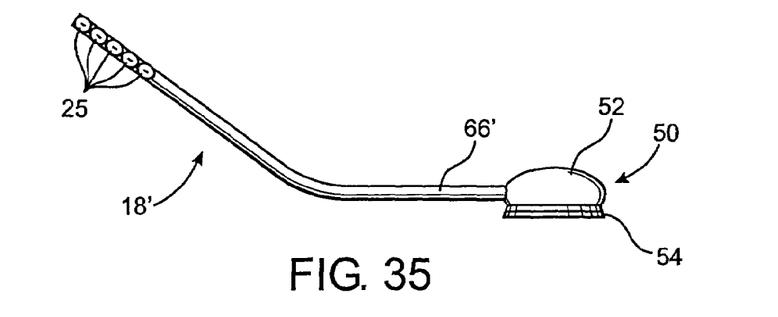
Figure 36:
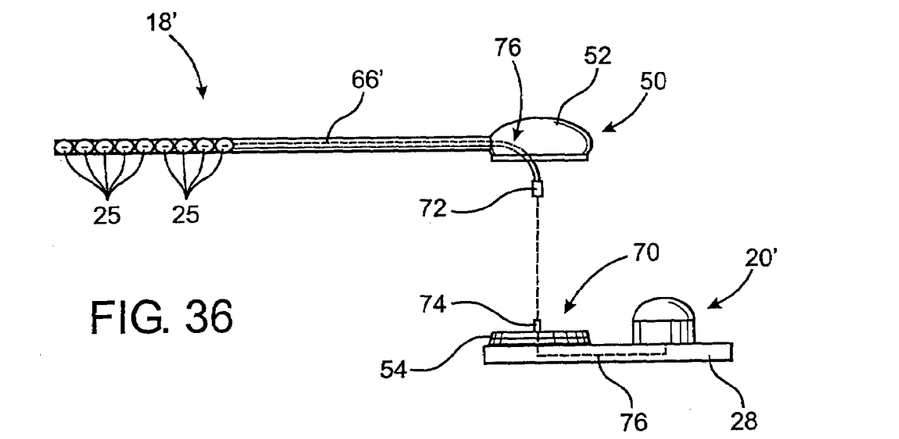
FIG. 36 is an exploded view showing yet another preferred embodiment of a light source and associated power supply of the illumination assembly of the present invention.

The embodiments of FIGS. 31 through 37 are directed to an extension assembly which is representative of yet another preferred embodiment of the light source 18 incorporated within the illumination assembly 10. More specifically the mount 50 may include the head or cap 52 being fixedly or movably secured to the base 54. In addition, an extension assembly includes an elongated extension arm 66 having a light source 18 secured thereto. In the embodiments of FIGS. 31 and 32 the light source 18 may include one or more LED's 25 secured adjacent or contiguous to the outer end of the extension neck 66. In the embodiments of FIGS. 33 through 35 the extension neck 66' may be modified to have a substantially linear configuration or alternatively an angular or arced configuration.

Further structural modification of the extension neck 66' includes the provision for mounting a plurality of LED's preferably in succession, along at least a portion of the length of the extension neck 66' in order to further facilitate the versatility and adaptability in illuminating a predetermined work area of the device on which the light source 18' is supported or connected. Further structural modifications, defining at least yet another preferred embodiment of the illumination assembly of the present invention are demonstrated in FIG. 36. More specifically, the extension neck 66' of the light source 18' is connected to the power supply 20' by means of an electrically coupling interface generally indicated as 70. The interface 70 includes a plug and receiving pin 72 and 74 respectively disposed and structured for detachable connection to one another wherein the power supply 20', including a contained battery is connected to the coupling interface pin 74 by appropriate conductors as at 76. The plug may be imbedded in or otherwise secured to the mount 50. Obviously the plug and the pin arrangement can be reversed such that the plug 72 is mounted on the support platform 28 in association with the base segment 54 rather than with the cap or head portion 52 of the mount 50.

Figure 37:
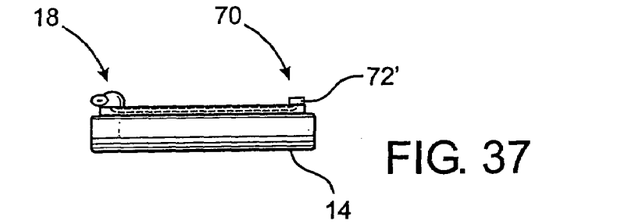
FIG. 37 is a side view of yet another preferred embodiment incorporating an electrical interface connection similar to the embodiment of FIG. 36.

Movable adjustment of the entire extension neck 66' can be readily accomplished in either a rotational, pivotal or reciprocal twisting movement as demonstrated with respect to the embodiment of FIG. 26 due at least in part to the interconnection between the base segment 54 and the head 52 as described with reference to FIG. 27 and the fact that the connecting conductors as at 76' are loosely disposed and/or are of sufficient length to accommodate the aforementioned diverse or universal type of movement. FIG. 37 represents yet another embodiment of the coupling interface as at 70' comprising a plug or receptor 72' disposed and structured to receive a cooperatively structured receptacle pin (not shown for purposes of clarity) which may be associated with an "external" power supply rather than the contained, cooperatively disposed power supply 20 normally directly associated with the light source 18.

With primary reference to FIGS. 38 through 42 additional preferred embodiments of the illumination assembly are disclosed therein which are distinguishable from the above-noted preferred embodiments of FIGS. 1 through 37. More specifically, the preferred embodiments of FIGS. 38 through 42 are distinguishable by being substantially integrated or "built-in" rather than being removably attached and/or mounted on various ones the plurality of devices 12' as described above. For purposes of consistency and clarity, each of the devices 12' referred to hereinafter will also be represented by a tweezer like structure. However, as with the other preferred embodiments set forth in FIGS. 1 through 37, the device 12' may be any of any of an extremely large number of utilitarian devices of the type, but not limited to, those devices set forth in the composite of FIG. 4. As such, the preferred embodiments of FIGS. 38 through 42, being integrated into the individual devices 121, are absent a mounting assembly 14 of the type set forth above with specific reference to the sleeve type mounting assembly 16 or the clamp assembly 40.

The illumination assembly generally indicated as 80 of the integrated category of preferred embodiments include a light source 82 comprising one or more light generating elements 82, wherein each of the light generating elements 82 are preferably in the form of an LED of the type set forth above. Similarly, the light source 82 may include an adjustable mount such as of the type indicated generally as 50 and including a base 54 and a head or cap portion 52. Such mount structure 50 may be structured to be a fixed one piece construction as demonstrated in the composite of FIG. 28 or may be universally movable as indicated by directional arrows 60 and 62 represented in FIG. 26. However, it should be noted that the light source 82 comprising one or more LED's may be otherwise structured to best accommodate its integrated inclusion within any one the plurality of devices 12' with which it is associated.

In that the ultimate goal is to accomplish a desired or maximum level of illumination of the work area of the device 12', such desired amount of illumination may be accomplished by providing a plurality of light sources and associated LED's in different, spaced apart and/or substantially adjacent portions of the device 12'. The desired illumination may also be accomplished by allowing the LED or other operative components of the light source 82 to be adjustable in order that the light source may be selectively positioned on the device 12' while the one or more LED's associated therewith may be selectively oriented relative to the work area of the device 12' and/or of the device itself.

Figure 38:
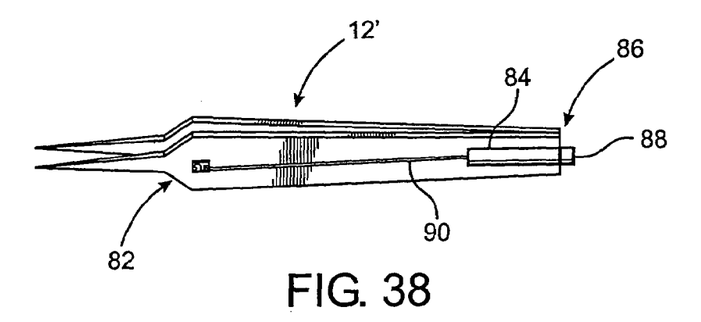
FIG. 38 is a perspective view of yet another preferred embodiment of illumination assembly of the present invention comprising an integrated or "built-in" construction.
Figure 39:
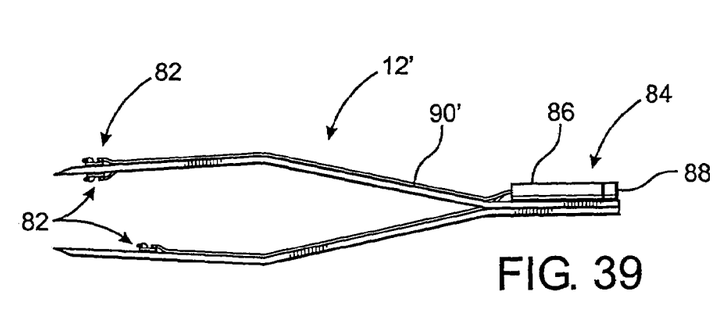
FIG. 39 is a side view of yet another preferred embodiment of the integrated modification of the illumination assembly of the present invention.

Accordingly, with reference to the embodiments of FIGS. 38 and 39, a power supply generally indicated as 84 is also integrated within the device 12' such as by including one or more replaceable batteries within a housing 86. A closure member 88 may be removably attached to the housing 86 in order to facilitate access to the interior thereof and to the batteries contained therein.

The power supply or batteries contained within the housing 86 is electrically connected to the light source to provide sufficient energy to activate the one or more LED's associated therewith. As such, one or more conductors 90 are located within the interior of appropriate interconnecting portions of the device 12, as shown in FIG. 38 or alternatively may be disposed along an exterior surface as at 90' in FIG. 39. In this latter embodiment the conductor 90' as well as certain other operative components of the light assembly 80 may be "integrated" into the device 12' by means of encapsulating the conductor 90' and/or other operative components within or beneath a dipped or molded plastic, rubber or like material outer coating. It is of course noted that the specific location or placement of the light sources 82, the conductors 90, 90' as well as the location, configuration and dimension of the housing 86 of the power supply 84 may vary dependant upon the physical characteristics and use of the particular device 12' with which the illumination assembly 80 is used.

Figures 40, 41:
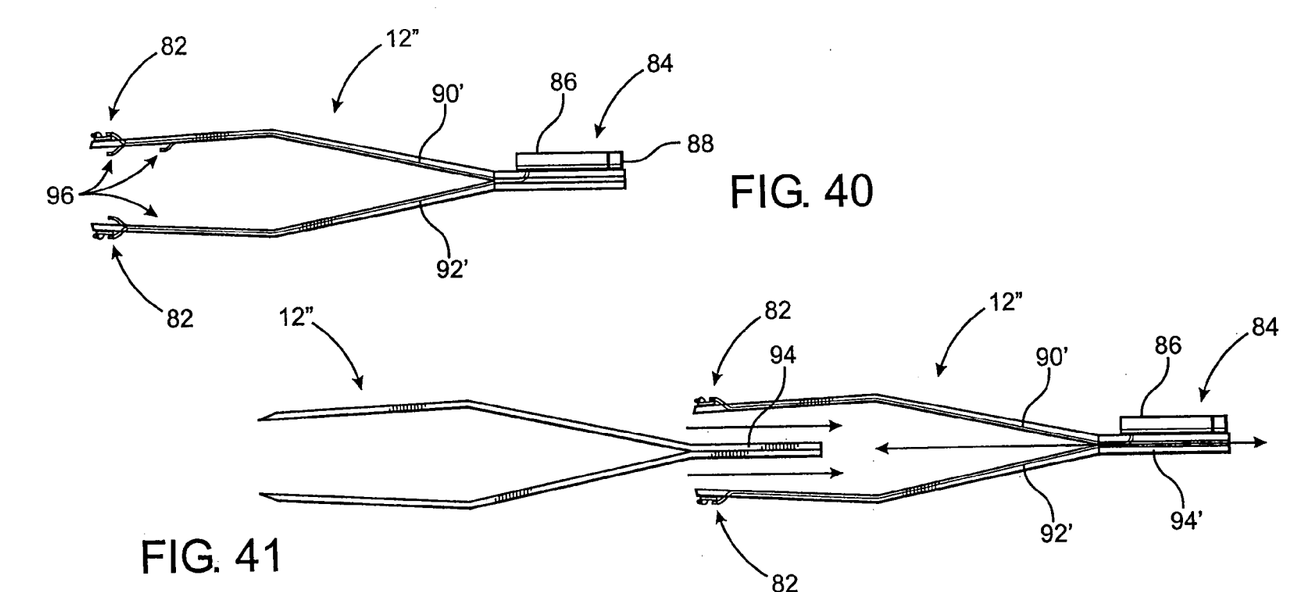
FIG. 40 is yet another preferred embodiment of the integrated structure of the illumination assembly of the present invention.
FIG. 41 is an exploded view of yet another preferred embodiment of the integrated structure of the illumination assembly of the present invention.
Figure 42:
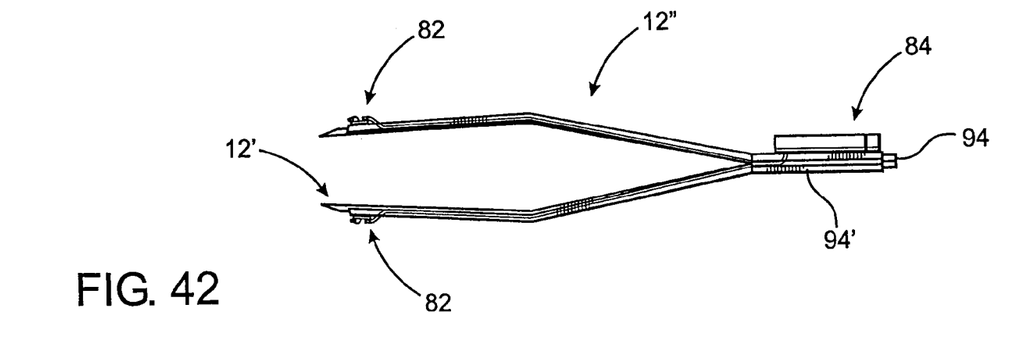
FIG. 42 is a side view in assembled form of the embodiment of FIG. 41.

With primary reference to FIGS. 40 through 42, yet another preferred embodiment included within the integrated category of illumination assemblies comprises a jacket or overlying covering generally indicated as 12". The jacket 12" will be formed from a moldable plastic or like material capable of being fabricated, using any appropriate means, to a size and configuration corresponding to that of the actual device 12'. FIG. 41 discloses the jacket or covering 12" in an unassembled position, wherein the indicated directional arrows are representative of the placement of the true device 12' into the jacket or shell assembly 12". In the specific representation where 12' is a tweezer type of structure, the head or stem 94 is received within a socket 94' of the shell 12" as clearly indicated. The power supply generally indicated as 84, including the housing 86 may be integrally or otherwise fixedly secured to the shell or jacket 12" as indicated. Similarly, one or more electrical conductors 90 are integrated within or otherwise fixedly secured to the various correspondingly disposed portions of the shell or jacket 12" in order to establish electrical connection between the power supply 84 and the one or more light sources 82. Specific mounting and securement of the shell or jacket 12" may be accomplished by a number of appropriate connecting means. One example thereof would be the provision of mounting or connecting tabs 96 secured to appropriate portions or surfaces of the shell 12" as clearly indicated in FIG. 40. Obviously other means of attachment may be utilized to facilitate a secure and sometimes permanently fixed integration of the shell or jacket 12" and the device 12'.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An illumination assembly usable with a device for illuminating a predetermined work area thereof, said illumination assembly comprising:
   a) a light source comprising a plurality of LED's, at least one of said LED's being adjustably positionable relative to a remainder of said plurality of LED's,
   b) a power supply electrically connected to said light source,
   c) a mounting assembly connected in supporting relation to at least said light source, and
   d) said mounting assembly structured to adjustably secure said light source on the device in a position which facilitates illumination of the predetermined work area.

2. An illumination assembly as recited in claim 1 wherein said mounting assembly is structured to adjustably secure said light source in any of a plurality of positions on the device so as to selectively vary the illumination of the predetermined work area.

3. An illumination assembly as recited in claim 1 wherein said mounting assembly is structured for movable and removable disposition of said light source on the device.

4. An illumination assembly usable with a device for illuminating a predetermined work area thereof, said illumination assembly comprising:
   a) a light source comprising at least one light generating element,
   b) a power supply electrically connected to said light source,
   c) a mounting assembly connected in supporting relation to at least said light source,
   d) said mounting assembly structured to adjustably secure said light on the device in a position which facilitates illumination of the predetermined work area, and
   e) an interface comprising a plug-in connector at least partially formed of conductive material and structured to detachably and electrically connect said power supply to said light source.

5. An illumination assembly usable with a device for illuminating a predetermined work area thereof, said illumination assembly comprising:
   a) a light source comprising a plurality of light generating elements,
   b) a power supply electrically connected to said light source,
   c) a mounting assembly connected in supporting relation to at least said light source,
   d) said mounting assembly structured to adjustably secure said light source on the device in a position which facilitates illumination of the predetermined work area,
   e) said light source further comprising an extension assembly extending outwardly from said mounting assembly and including an elongated neck and a mount secured to one end of said neck, and
   f) said plurality of light generating elements extending along the length of said neck in outwardly spaced relation to said mounting assembly.

6. An illumination assembly usable with any one of a plurality of devices for illuminating a predetermined work area of the device, said illumination assembly comprising:
   a) a mounting assembly movably and removably connected to the device,
   b) a light source comprising at least one LED supported on the mounting assembly and movable therewith relative to the device,
   c) a power supply supported on the mounting assembly and electrically connected to said light source,
   d) said light source and said mounting assembly cooperatively structured to facilitate adjustable positioning of said light source on the device and selective orientation of said LED relative to the work area of the device,
   e) said light source further comprising an extension assembly including a neck extending outwardly from said mounting assembly, and
   f) said light source further comprising a plurality of LED'S extending continuously along a length of said neck in outwardly spaced relation to said mounting assembly.

7. An illumination assembly as recited in claim 1 wherein said one LED is movably interconnected to said mounting assembly and selectively positionable along at least a relatively transverse axes.

8. An illumination assembly as recited in claim 1 wherein said light source comprises a connector member interconnecting said one LED in outwardly spaced relation to said mounting assembly.

9. An illumination assembly as recited in claim 8 wherein said connector member comprises an elongated configuration and is at least partially formed from a pliable material.

10. An illumination assembly as recited in claim 9 wherein said connector member comprises an electrical conductor between said one LED and said power supply.

11. An illumination assembly as recited in claim 1 wherein said power supply is supported on said mounting assembly substantially adjacent to said light one LED.

12. An illumination assembly as recited in claim 1 further comprising a support platform secured to said mounting assembly in supporting relation to both said light source and said power supply.

13. An illumination assembly as recited in claim 4 wherein said light source comprises a plurality of light generating elements, each of which are respectively interconnected to said power supply by said interface.

14. An illumination assembly as recited in claim 5 wherein said light source comprises at least one light generating element disposed on said neck substantially adjacent an outer portion thereof.

15. An illumination assembly as recited in claim 5 wherein said neck comprises a substantially angular configuration along at least a portion of its length.

16. An illumination assembly usable with any one of a plurality of devices for illuminating a predetermined work area of the device, said illumination assembly comprising:
   a) amounting assembly movably and removably connected to the device,
   b) a light source comprising a plurality of LED's, at least one of said plurality of LED's supported on the mounting assembly and movable therewith relative to the device,
   c) a power supply supported on the mounting assembly and electrically connected to said light source, and
   d) said light source and said mounting assembly cooperatively structured to facilitate adjustable positioning of said light source on the device, at least one LED movable relative to a remainder of said plurality of LED's, into a plurality of different illuminating orientations relative to the work area of the device.

17. An illumination assembly as recited in claim 16 wherein said mounting assembly comprises a sleeve having a peripheral wall terminating in opposite open ends and disposed in surrounding relation to a hollow interior of said sleeve.

18. An illumination assembly as recited in claim 17 wherein said sleeve is formed of a flexible, at least partially resilient material and is disposable in surrounding relation to substantially correspondingly dimensioned portions of the device.

19. An illumination assembly as recited in claim 17 wherein said sleeve is formed of at least partially rigid material.

20. An illumination assembly as recited in claim 1 wherein said mounting assembly comprises a sleeve having a peripheral wall terminating in opposite, open ends and disposed in surrounding relation to a hollow interior of said sleeve.

21. An illumination assembly as recited in claim 20 wherein said sleeve is formed of a flexible material and is disposable in surrounding relation to a substantially correspondingly dimensioned portion of the device.

22. An illumination assembly as recited in claim 21 wherein said sleeve is formed of an at least partially resilient material.

23. An illumination assembly as recited in claim 20 wherein said sleeve is formed of an at least partially rigid material.

24. An illumination assembly as recited in claim 20 wherein said peripheral wall comprises a closed, continuous configuration between said opposite open ends thereof.

25. An illumination assembly as recited in claim 20 wherein said peripheral wall further comprises an access opening formed along a length thereof and a closure assembly disposed along a length of said access opening.

26. An illumination assembly as recited in claim 25 wherein said access opening and said closure assembly are cooperatively disposed and structured to orient said peripheral wall between an open position and a closed position.

27. An illumination assembly as recited in claim 26 wherein said open position is at least partially defined by substantially transverse placement of the device through said access opening and into said hollow interior.

28. An illumination assembly as recited in claim 20 wherein said light source is disposed on an exterior of said sleeve and movable therewith relative to the device.

29. An illumination assembly as recited in claim 16 wherein said mounting assembly comprises a clamp assembly including a platform and a plurality of flanges extending outwardly therefrom, a biasing structure disposed in biasing relation to said flanges and structured to normally force said flanges into gripping engagement with the device.

30. An illumination assembly as recited in claim 1 wherein said mounting assembly comprises a clamp assembly including a platform and a plurality of flanges extending outwardly from said platform and at least partially movable relative thereto, said flanges disposable in gripping, at least partially enclosing relation to the device.

31. An illumination assembly as recited in claim 30 wherein said clamp assembly further comprises a biasing structure disposed in biasing relation to said flanges and structured to normally force said flanges into said gripping engagement with the device.

32. An illumination assembly as recited in claim 31 wherein said biasing structure comprises a spring member connected in biasing relation to said flanges.

33. An illumination assembly as recited in claim 31 wherein said biasing structure is inherently formed in said clamp assembly and is at least partially defined by a configuration of said platform and said flanges and a material from which said platform and said flanges are formed.

34. An illumination assembly as recited in claim 30 wherein said platform comprises a housing, wherein at least said power supply is mounted on said housing.

35. An illumination assembly as recited in claim 34 wherein both said light source and said power supply are mounted on said housing.

36. An illumination assembly as recited in claim 35 wherein said housing comprises an at least partially hollow interior, said one light generating element and said power supply mounted adjacent opposite ends of said housing.

37. An illumination assembly as recited in claim 34 wherein said light source is mounted on said platform is spaced relation to said housing.

38. An illumination assembly as recited in claim 37 wherein said plurality of LED's are mounted on said platform, at least one of said LED's being selectively adjustable relative to said clamp assembly.

39. An illumination assembly as recited in claim 16 wherein said one LED is both rotationally and pivotally connected to said mounting assembly.

* * * * *